(12) United States Patent
Fortson

(10) Patent No.: US 10,806,439 B2
(45) Date of Patent: Oct. 20, 2020

(54) SUTURE-BASED CLOSURE WITH HEMOSTATIC TRACT PLUG

(71) Applicant: Abbott Cardiovascular Systems, Inc., Santa Clara, CA (US)

(72) Inventor: Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 194 days.

(21) Appl. No.: 15/697,842

(22) Filed: Sep. 7, 2017

(65) Prior Publication Data

US 2017/0360421 A1 Dec. 21, 2017

Related U.S. Application Data

(63) Continuation of application No. 15/090,247, filed on Apr. 4, 2016, now Pat. No. 9,757,108, which is a
(Continued)

(51) Int. Cl.
*A61B 17/04* (2006.01)
*A61B 17/00* (2006.01)
(Continued)

(52) U.S. Cl.
CPC ...... *A61B 17/0057* (2013.01); *A61B 17/0401* (2013.01); *A61B 17/0469* (2013.01);
(Continued)

(58) Field of Classification Search
CPC ............ A61B 17/0469; A61B 17/0401; A61B 2017/0409; A61B 2017/0472;
(Continued)

(56) References Cited

U.S. PATENT DOCUMENTS

| 5,304,184 A | 4/1994 | Hathaway et al. |
| 5,417,699 A | 5/1995 | Klein et al. |

(Continued)

FOREIGN PATENT DOCUMENTS

| WO | WO 1994013211 | 6/1994 |
| WO | WO 1998042262 | 10/1998 |

(Continued)

OTHER PUBLICATIONS

U.S. Appl. No. 09/866,551, filed May 25, 2001, Ginn.
(Continued)

*Primary Examiner* — George J Ulsh
(74) *Attorney, Agent, or Firm* — Workman Nydegger; Randy Shen

(57) ABSTRACT

Devices for closing a passage through tissue communicating with a body lumen. The device may include an elongate body, a sheath disposed at the distal end of the device for disposition within a body lumen, a hollow needle disposed within a needle lumen of the body, the needle being selectively advancable through the needle lumen, a suture-anchor ejection mandrel disposed within the hollow needle that is also selectively advancable through the hollow needle, a suture-anchor and suture disposed within the hollow needle, a distal end of the suture attached to the suture anchor for ejection out the hollow needle by the mandrel. A needle guide disposed between the sheath and proximal end of the body may include a needle port through which the needle can exit. A hemostatic plug is disposed over the needle port so as to be penetrated by the needle upon exiting the port.

19 Claims, 15 Drawing Sheets

Related U.S. Application Data continuation of application No. 14/052,654, filed on Oct. 11, 2013, now Pat. No. 9,301,746.

(51) Int. Cl.
*A61B 17/06* (2006.01)
*A61B 17/22* (2006.01)

(52) U.S. Cl.
CPC  *A61B 17/06066* (2013.01); *A61B 2017/0065* (2013.01); *A61B 2017/00623* (2013.01); *A61B 2017/00663* (2013.01); *A61B 2017/00672* (2013.01); *A61B 2017/00778* (2013.01); *A61B 2017/0404* (2013.01); *A61B 2017/0409* (2013.01); *A61B 2017/0417* (2013.01); *A61B 2017/0427* (2013.01); *A61B 2017/0464* (2013.01); *A61B 2017/0472* (2013.01); *A61B 2017/0496* (2013.01); *A61B 2017/061* (2013.01); *A61B 2017/22038* (2013.01)

(58) Field of Classification Search
CPC .......... A61B 2017/00778; A61B 17/34; A61B 17/0057; A61B 2017/00637; A61B 2017/00641; A61B 17/085; A61B 17/0482; A61B 17/07292; A61B 2017/00623

See application file for complete search history.

(56) References Cited

U.S. PATENT DOCUMENTS

| | | | |
|---|---|---|---|
| 5,476,469 | A | 12/1995 | Hathaway et al. |
| 5,613,974 | A | 3/1997 | Andreas et al. |
| 5,690,671 | A | 11/1997 | McGurk et al. |
| 5,720,757 | A | 2/1998 | Hathaway et al. |
| 5,759,173 | A | 6/1998 | Preissman et al. |
| 5,776,099 | A | 7/1998 | Tremulis |
| 5,779,719 | A | 7/1998 | Klein et al. |
| 5,810,850 | A | 9/1998 | Hathaway et al. |
| 5,817,057 | A | 10/1998 | Berenstein et al. |
| 6,036,699 | A | 3/2000 | Andreas et al. |
| 6,132,440 | A | 10/2000 | Hathaway et al. |
| 6,136,010 | A | 10/2000 | Modesitt et al. |
| 6,197,042 | B1 | 3/2001 | Ginn et al. |
| 6,348,059 | B1 | 2/2002 | Hathaway et al. |
| 6,355,050 | B1 | 3/2002 | Andreas et al. |
| 6,391,048 | B1 | 5/2002 | Ginn et al. |
| 6,461,364 | B1 | 10/2002 | Ginn et al. |
| 6,558,349 | B1 | 5/2003 | Kirkman |
| 6,726,704 | B1 | 4/2004 | Loshakove et al. |
| 6,780,197 | B2 | 8/2004 | Roe et al. |
| 6,942,674 | B2 | 9/2005 | Belef et al. |
| 6,964,668 | B2 | 11/2005 | Modesitt et al. |
| 7,060,084 | B1 | 6/2006 | Loshakove et al. |
| 7,063,711 | B1 | 6/2006 | Loshakove et al. |
| 7,235,087 | B2 | 6/2007 | Modesitt et al. |
| 7,842,068 | B2 | 11/2010 | Ginn |
| 7,850,701 | B2 | 12/2010 | Modesitt |
| 8,038,688 | B2 | 10/2011 | Modesitt et al. |
| 8,057,491 | B2 | 11/2011 | Modesitt et al. |
| 8,133,238 | B2 | 3/2012 | Maruyama et al. |
| 8,137,364 | B2 | 3/2012 | Zung et al. |
| 8,241,323 | B2 | 8/2012 | Kawaura et al. |
| 8,764,795 | B2 | 7/2014 | Whitman et al. |
| 9,050,065 | B2 | 6/2015 | Whitman et al. |
| 9,138,211 | B2 | 9/2015 | Whitman |
| 9,265,497 | B2 | 2/2016 | Teichman et al. |
| 9,301,746 | B2 | 4/2016 | Fortson |
| 9,427,220 | B2 | 8/2016 | Whitman et al. |
| 9,757,108 | B2 | 9/2017 | Fortson |
| 2004/0087985 | A1 | 5/2004 | Loshakove et al. |
| 2004/0092964 | A1 | 5/2004 | Modesitt et al. |
| 2004/0092973 | A1 | 5/2004 | Chanduszko et al. |
| 2005/0283188 | A1 | 12/2005 | Loshakove et al. |
| 2006/0287674 | A1 | 12/2006 | Ginn et al. |
| 2008/0132943 | A1 | 6/2008 | Maiorino et al. |
| 2008/0287967 | A1 | 11/2008 | Andreas et al. |
| 2008/0319458 | A1 | 12/2008 | Reynolds |
| 2009/0088779 | A1 | 4/2009 | Zung et al. |
| 2010/0179567 | A1 | 7/2010 | Voss et al. |
| 2010/0179571 | A1 | 7/2010 | Voss |
| 2010/0179572 | A1 | 7/2010 | Voss et al. |
| 2010/0179589 | A1 | 7/2010 | Roorda et al. |
| 2010/0179590 | A1 | 7/2010 | Fortson et al. |
| 2011/0106148 | A1 | 5/2011 | Ginn et al. |
| 2011/0218568 | A1 | 9/2011 | Voss |
| 2011/0288563 | A1 | 11/2011 | Gianotti et al. |
| 2012/0016384 | A1 | 1/2012 | Wilke et al. |
| 2012/0089159 | A1 | 4/2012 | Shluzas |
| 2013/0211426 | A1 | 8/2013 | Whitman et al. |
| 2013/0211450 | A1 | 8/2013 | Whitman |
| 2014/0039548 | A1 | 2/2014 | Whitman et al. |
| 2014/0236189 | A1 | 8/2014 | Melsheimer et al. |
| 2015/0119906 | A1 | 4/2015 | Bagaoisan et al. |
| 2015/0359627 | A1 | 12/2015 | Whitman |
| 2016/0095704 | A1 | 4/2016 | Whitman |

FOREIGN PATENT DOCUMENTS

| | | |
|---|---|---|
| WO | WO 2000051498 | 9/2000 |
| WO | WO 2001049186 | 7/2001 |
| WO | WO 2002045594 | 6/2002 |
| WO | WO 2003071956 | 9/2003 |
| WO | WO 2003099134 | 12/2003 |
| WO | WO 2005023119 | 3/2005 |
| WO | WO 2005025430 | 3/2005 |
| WO | WO 2010081101 | 7/2010 |
| WO | WO 2010081102 | 7/2010 |
| WO | WO 2010081103 | 7/2010 |
| WO | WO 2010081106 | 7/2010 |
| WO | WO 2003047434 | 6/2013 |

OTHER PUBLICATIONS

U.S. Appl. No. 12/113,092, filed Apr. 30, 2008, Ginn et al.
U.S. Appl. No. 61/143,751, filed Jan. 9, 2009, Voss et al.
U.S. Appl. No. 14/052,654, dated Dec. 9, 2015, Notice of Allowance.
U.S. Appl. No. 15/090,247, dated Jun. 13, 2017, Notice of Allowance.

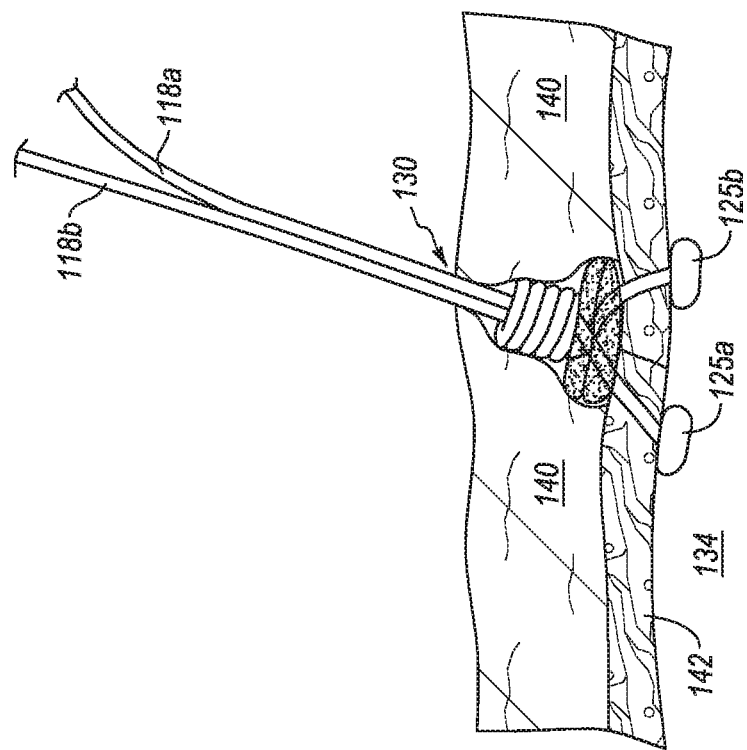
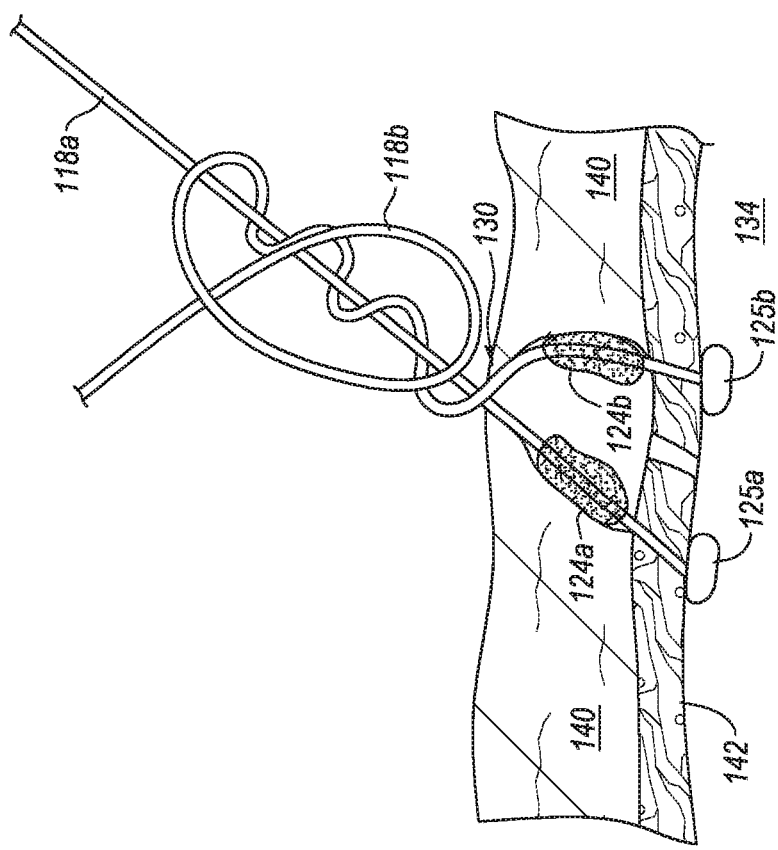

SUTURE-BASED CLOSURE WITH HEMOSTATIC TRACT PLUG

CROSS-REFERENCE TO RELATED APPLICATIONS

This is a continuation application of U.S. patent application Ser. No. 15/090,247, filed Apr. 4, 2016, entitled "Suture-Based Closure with Hemostatic Track Plug", which is a continuation application of U.S. patent application Ser. No. 14/052,654, filed Oct. 11, 2013, U.S. Pat. No. 9,301,746, entitled "Suture-Based Closure with Hemostatic Track Plug", the disclosures of which are incorporated herein by this reference.

BACKGROUND

The present invention relates generally to apparatus and methods for the closing of an access passage opened within a body lumen. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudoaneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

While other techniques, including use of fasteners, suturing, etc. have been proposed, existing approaches continue to exhibit limitations. For example, effective suture based vessel closure can be difficult due to the need to target suture capture for retrieval through the artery or other body lumen wall, which requires complicated mechanisms, such as that described in U.S. Publication 2009/0088779, herein incorporated by reference. In addition, a high level of practitioner skill is needed to maintain proper suture deployment angles for suture delivery and harvest. Even when performed properly, such procedures may still result in minor oozing from the access tract. The present disclosure addresses at least some of the presently existing disadvantages.

BRIEF SUMMARY

The present disclosure describes devices, systems, and methods for closing an access passage through tissue communicating with a body lumen. The device may include an elongate device body extending from a proximal end to a distal end, a sheath disposed at the distal end of the device for disposition within a body lumen during use, and at least one hollow needle disposed within a corresponding needle lumen of the elongate body. The hollow needle is advanceable through the needle lumen. A suture-anchor ejection mandrel is disposed within the hollow needle, which mandrel is also selectively advanceable through the hollow needle. A suture-anchor and suture may be disposed within the hollow needle, a distal end of the suture being attached to the suture-anchor for ejection out a distal end of the hollow needle by the mandrel.

The device may further comprise a needle guide disposed between the sheath and the proximal end of the device body. The needle guide may include a needle port corresponding to each hollow needle through which the hollow needles may exit the device during use. A hemostatic plug may be disposed over the needle port, within a receiving recess disposed about each needle port. As a result, the hemostatic plug may be penetrated by the hollow needle upon its exit through the needle port. The device may further comprise a needle advancement assembly disposed on or within the elongate body configured to selectively advance and deploy the hollow needle through the needle port and into tissue adjacent the access passage during use. A suture-anchor ejection assembly disposed on or within the elongate body may be configured to selectively advance the suture-anchor ejection mandrel so as to eject the suture-anchor from the hollow needle into the body lumen (e.g., an artery) at a location adjacent a wall of the body lumen in preparation for closing the access passage.

In another embodiment, the device may include an elongate device body extending from a proximal end to a distal end, a sheath disposed at the distal end of the device for disposition within a body lumen during use, and a pair of hollow needles disposed within corresponding needle lumens of the elongate body. Each hollow needle is advanceable through a corresponding one of the needle lumens. A suture-anchor ejection mandrel is disposed within each hollow needle, each mandrel being selectively advanceable through its corresponding hollow needle. A suture-anchor and suture may be disposed within each hollow needle, a distal end of each suture being attached to the suture-anchor for ejection out a distal end of the corresponding hollow needle by its corresponding mandrel.

The device may further comprise a needle guide disposed between the sheath and the proximal end of the device body. The needle guide may include a pair of needle ports, each port corresponding to a hollow needle through which the corresponding hollow needle may exit during use. Hemostatic plugs may be disposed over the needle ports, within receiving recesses disposed about each needle port so as to be penetrated by a corresponding hollow needle upon advancement. The device may further comprise a needle advancement assembly disposed on or within the elongate body configured to selectively deploy the hollow needles through the needle ports and into tissue adjacent the access passage during use. A suture-anchor ejection assembly disposed on or within the elongate body may be configured to selectively advance the suture-anchor ejection mandrels so as to eject the suture-anchors from the hollow needles and into the body lumen (e.g., an artery) at locations adjacent a wall of the body lumen in preparation for closing the access passage.

In another embodiment, the device may include an elongate device body extending from a proximal end to a distal end, a sheath disposed at the distal end of the device for disposition within a body lumen during use, and a pair of hollow needles (an anterior needle and a posterior needle) disposed within corresponding needle lumens of the elongate body. Each hollow needle is advanceable through a corresponding one of the needle lumens. A pair of suture-anchor ejection mandrels are also provided, with a mandrel disposed within each hollow needle, each mandrel being selectively advanceable through its corresponding hollow needle. A suture-anchor and suture may be disposed within each hollow needle, a distal end of each suture being attached to the suture-anchor for ejection out a distal end of the corresponding hollow needle by its corresponding mandrel.

The device may further comprise a needle guide disposed between the sheath and the proximal end of the device body. The needle guide may include anterior and posterior needle ports through which the corresponding anterior and posterior hollow needles may exit upon their advancement during use. The anterior needle port may be disposed anterior (i.e., distally) relative to the posterior needle port along the needle guide. Hemostatic plugs may be disposed over each needle port, within receiving recesses disposed about each needle port so as to be penetrated by a corresponding hollow needle upon advancement. The device may further comprise a needle advancement assembly disposed on or within the elongate body configured to selectively deploy the hollow needles through the needle ports and into tissue adjacent the access passage during use. A suture-anchor ejection assembly disposed on or within the elongate body may be configured to selectively advance the suture-anchor ejection mandrels so as to eject the suture-anchors from the hollow needles into the body lumen, to locations adjacent a wall of the body lumen in preparation for closing the access passage.

The needle advancement assembly, the suture-anchor ejection assembly, the suture-anchor ejection mandrels, and the hollow needles may be together detachable from the distal end of the device body to allow a user to remove these proximally disposed structures once suture-anchors have been deployed and set, providing the practitioner with easy access to the remaining device structure and the proximal ends of the sutures in preparation for closing the access passage.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIGS. 9A-9B illustrate tying and sliding of a surgical sliding knot formed with the suture legs to close the access tract, the hemostatic plugs engaged by the suture legs providing a secondary sealing mechanism for ensuring effective closure of the access tract.

DETAILED DESCRIPTION

Introduction

Figure 1:
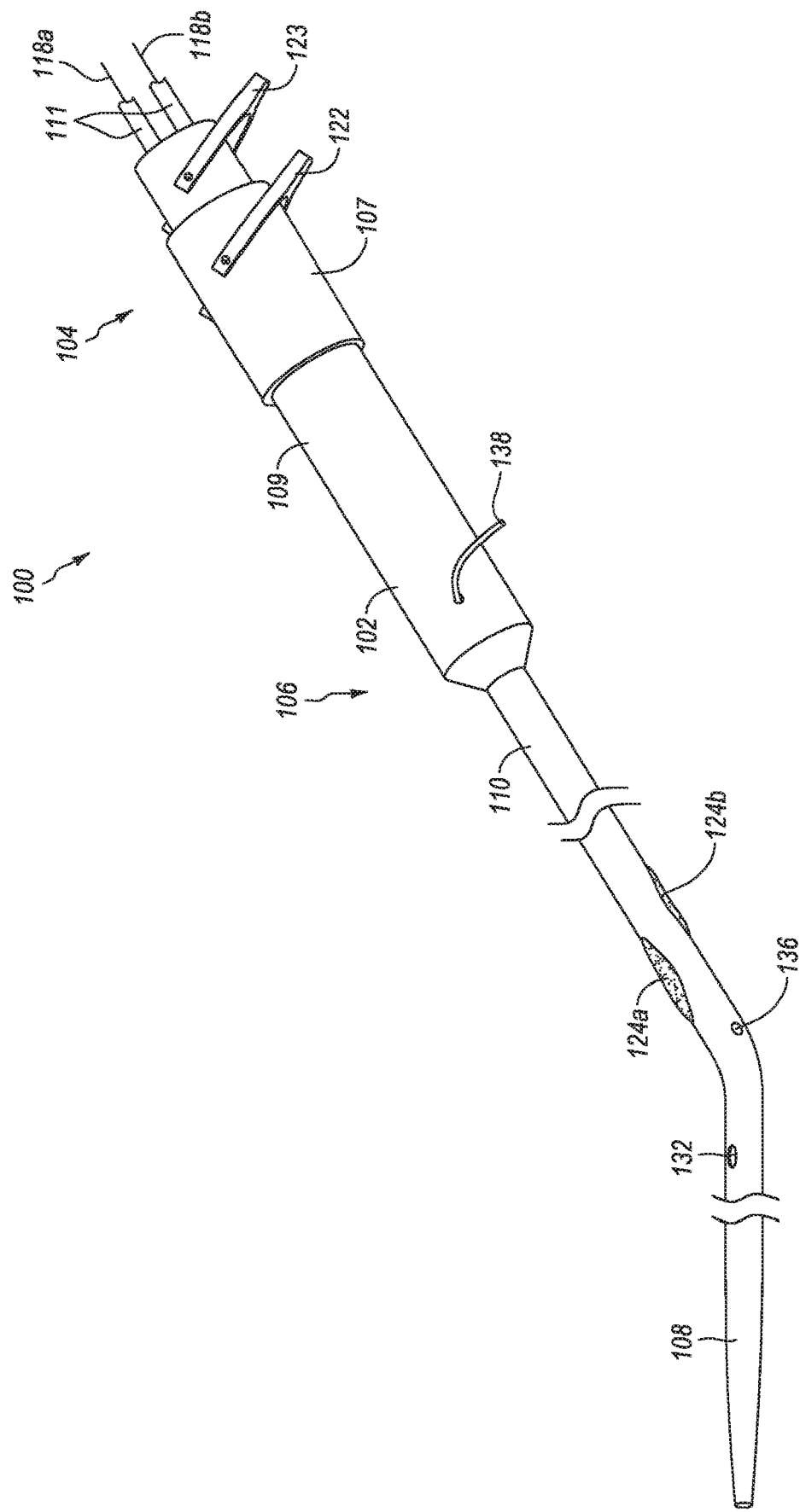
FIG. 1 is an isometric view of an exemplary closure device according to an embodiment of the present disclosure.
Figure 2:
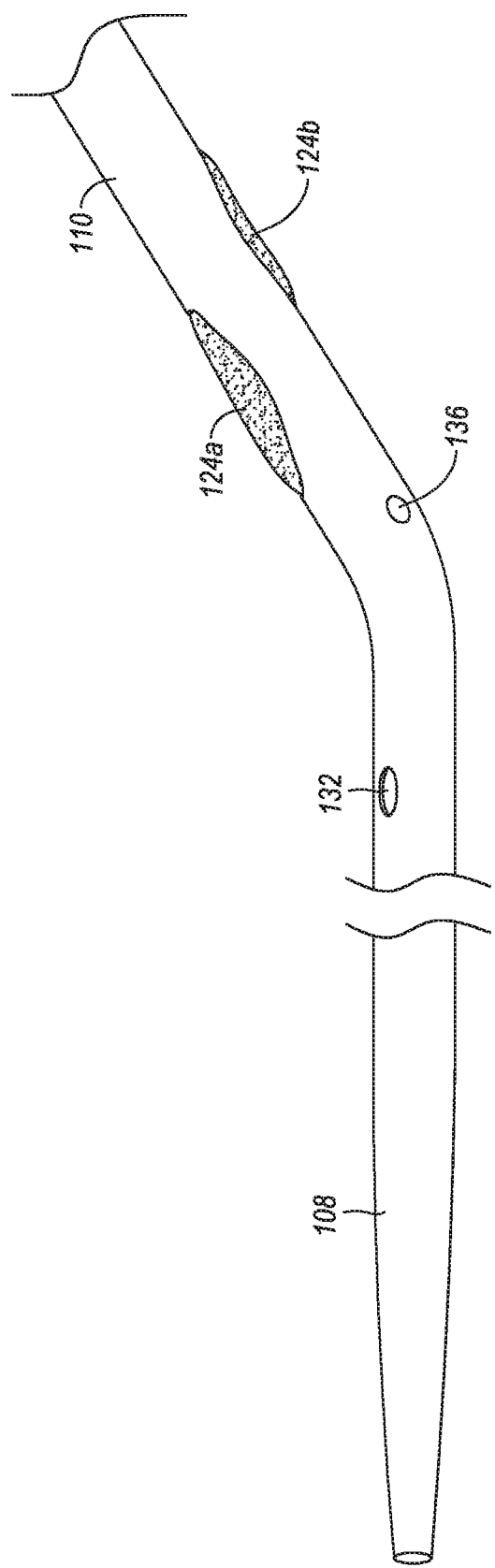
FIG. 2 is a close-up view showing the distal sheath and needle guide of the device of FIG. 1.

In one aspect, the present disclosure describes devices for closing an access tract or passage through tissue communicating with a body lumen. The device may include an elongate body extending from a proximal end to a distal end, a sheath disposed at the distal end of the device for disposition within a body lumen during use, at least one hollow needle disposed within a corresponding needle lumen of the body, at least one suture-anchor ejection mandrel disposed within the hollow needle, a suture-anchor and suture disposed within the hollow needle, a needle guide including a needle port disposed between the sheath and proximal end of the elongate body, a hemostatic plug disposed over the needle port, within a receiving recess disposed about the needle port, and advancement and ejection assemblies on or within the elongate body for deploying the hollow needle(s) and ejecting the suture-anchor ejection mandrel, respectively.

Each suture-anchor ejection mandrel is disposed within a corresponding hollow needle so that both the needle(s) and mandrel(s) are selectively advanceable upon activation of the associated advancement and ejection assemblies, respectively. The hollow needle can advance through the needle lumen in the elongate body, so as to exit through the needle port of the needle guide, while the mandrel is selectively advanceable within the hollow needle, so as to allow the suture-anchor stored therein to be ejected out, when desired. The hemostatic plugs are disposed over the needle port(s) so that when exiting the needle port, a respective hollow needle penetrates the hemostatic plug disposed thereover. The suture-anchor may be pushed out distal end of the hollow needle, while the suture attached to the suture-anchor trails behind, inside the hollow needle. Upon retraction of the hollow needle and mandrel (while the suture-anchor and suture remain in place), the suture and plug become engaged together.

An exemplary device may include two hollow needles, and two associated mandrels, needle ports, hemostatic plugs, suture-anchors, and sutures. The device allows a practitioner to position the device within the passage to be closed, the hollow needles are advanced, penetrating the hemostatic plug and into tissue surrounding the access tract, penetrating into the artery or other body lumen. The mandrels are then advanced, ejecting the suture-anchors through the hollow needles into the artery or other body lumen. The suture anchors may be positioned adjacent the wall of the body lumen by tensioning the proximal end of each suture, so as to "set" the suture-anchors in a desired position (e.g., one suture-anchor on either side of the opening). The proximal "back end" portion of the device, including the hollow needles and mandrels may then be withdrawn, providing engagement between the sutures and the hemostatic plugs (e.g., within the access passage) as the plugs close about the suture as the needle is withdrawn and the suture remains in place. The distal "front end" portion of the device may be partially withdrawn to the point that the sheath continues to provide hemostasis of the opening, and the sutures may then be tied down. Because the suture legs include the hemostatic plugs engaged therewith, as the suture legs are tied down over the access opening, the hemostatic plugs provide additional sealing of the opening beyond that provided by suturing alone.

Where two or more suture-anchors are deployed (e.g., one on each side of the opening) through a corresponding number of hollow needles, closure of the opening is more effective than methods that deliver only a single fastener, plug, or suture (e.g., centered over the opening). When delivering such fasteners, plugs, etc. over the opening, it can be difficult to ensure that the fastener or plug is properly placed. Locating the plug or fastener too far from the interface of overlying tissue and the adventitial surface of the blood vessel or other body lumen can result in failure to provide hemostasis and other problems. It is also possible that the fastener or plug may undesirably intrude into the body lumen, resulting in intravascular clots and other problems.

In addition, as compared to existing closure techniques that deliver a suture so as to cross the opening (e.g., using dual needles), the present techniques are simpler, as it is not necessary to retrieve the distal end of the suture once it is delivered through the wall of the body lumen. This results in a significantly simpler closure technique that can be practiced without the high level of practitioner skill needed to maintain proper suture deployment angles for delivery and subsequent retrieval. The use of suture-anchors attached to the distal end of the sutures allows them to be delivered to opposing sides of the opening (no retrieval needed), after which the proximal ends of the sutures may be tied together, forming a closing seal over the opening. Because the suture legs include hemostatic plugs engaged or anchored thereto, the plugs aid in ensuring that an effective seal is formed, which may effectively reduce or eliminate tract ooze from the access site.

While the suture-anchors may remain within the body lumen following closure, they may be formed of a rapidly-eroding material that dissolves within the body lumen within a matter of hours.

II. Exemplary Devices and Methods

Referring to FIG. 1, an isometric view of an example of a device 100 for closing an access passage through tissue that embodies features of the invention is illustrated. Device 100 may include an elongate body 102 extending from a proximal end 104 to a distal end 106. A sheath 108 may be disposed at distal end 106 of device 100 for disposition into a body lumen (e.g., an artery) during use. Device 100 may further include a needle guide 110 disposed between sheath 108 and the proximal end 104 of body 102. Needle guide 110 may be considered part of elongate body 102.

Figure 4:
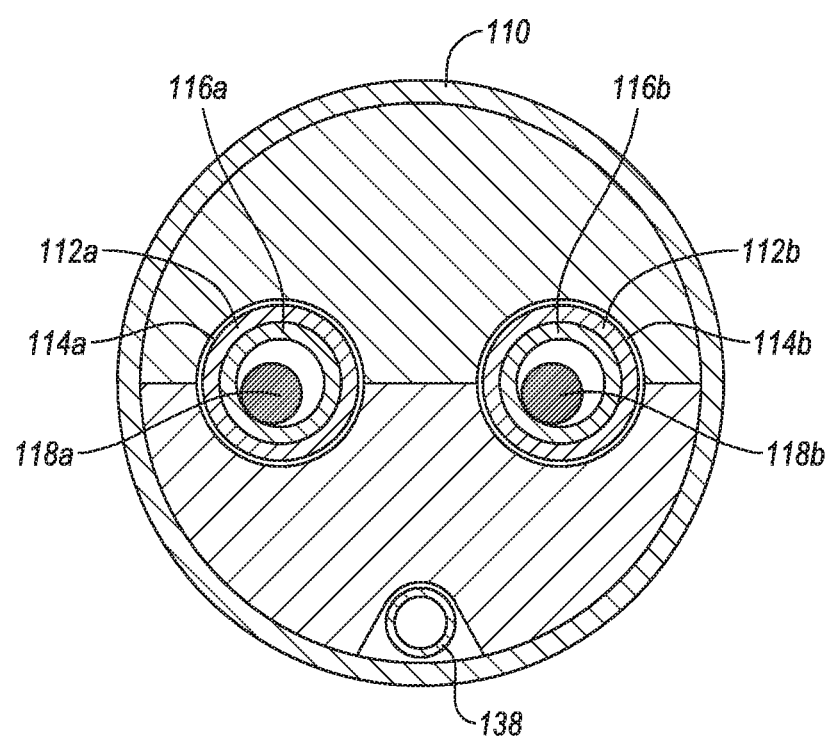
FIG. 4 is a transverse cross-sectional view through the needle guide portion of the device of FIG. 1.

Disposed on or within device 100 are various structures that aid in delivering a suture to close the access passage. Some such structures discussed below may perhaps be best seen in FIG. 4, showing a transverse cross-section through needle guide 110. At least one hollow needle (e.g., anterior and posterior needles 112a and 112b) may be disposed within a corresponding needle lumen (e.g., lumens 114a, 114b) of needle guide 110. Such needle lumens may extend proximally from needle guide 110 into the proximal portions of body 102. At least one suture-anchor ejection mandrel (e.g., anterior and posterior mandrels 116a and 116b) may be disposed within the hollow needle(s). The one or more hollow needles (e.g., 112a, 112b) are selectively advanceable through the needle lumens 114a, 114b. The one or more mandrels (e.g., 116a, 116b) are selectively advanceable through the corresponding hollow needles (e.g., 112a, 112b) within which they are disposed. A suture-anchor and corresponding suture (e.g., sutures 118a, 118b) may also be disposed within the at least one hollow needle. A distal end of the suture may be attached to the suture-anchor so that when the suture-anchor is ejected out the distal end of a given hollow needle by the corresponding suture-anchor ejection mandrel, the attached suture may trail behind. In the illustrated embodiment, sutures 118a and 118b are shown received within a channel formed in mandrels 116a, 116b, although other configurations may of course be employed. For example, in another embodiment, the suture may be disposed within a groove formed in the exterior surface of mandrel 116a, 116b, a groove formed into an interior surface of hollow needle 112a, 112b, or simply disposed within a clearance space provided between mandrel 116a, 116b and corresponding hollow needle 112a, 112b. Other configurations may also be suitable for use. As shown in FIG. 1, the proximal end of the suture legs may reside and be stored within body 102 and/or suture lumens 111.

In an embodiment, sutures 118a, 118b may have a diameter from about 0.005 inch to about 0.015 inch (e.g., about 0.009 inch). Needle guide 110 may have a diameter from about 0.08 inch to about 0.15 inch (e.g., about 0.114 inch).

Figure 3A:
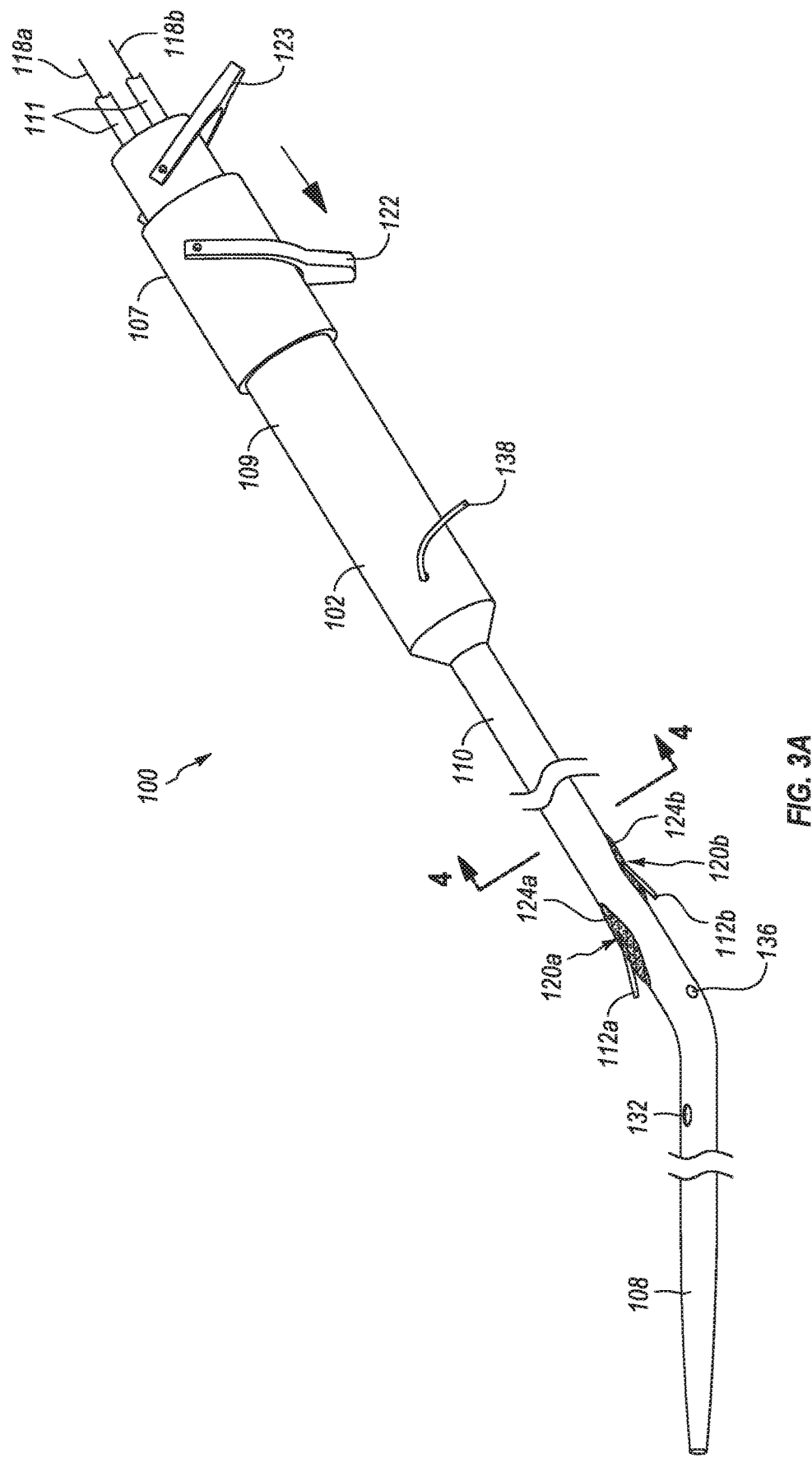
FIG. 3A is an isometric view of the device of FIG. 1, showing activation of the needle advancement assembly and associated deployment of the hollow needles through the needle ports.

Needle guide 110 includes at least one needle port through which the hollow needles exit during use. For example, in the illustrated configuration, two needle ports 120a and 120b may be provided, through which anterior hollow needle 112a and posterior needle 112b, respectively, may exit or protrude when needles 112a, 112b are deployed. FIG. 3A shows activation of a needle advancement assembly (e.g., a plunger, mandrel, or other mechanism operatively coupling needle advancement lever 122 with needles 112a, 112b), causing hollow needles 112a and 112b to be advanced distally, deploying through needle ports 120a and 120b. Because of placement of hemostatic plugs 124a and 124b over ports 120a and 120b, needles 112a, 112b penetrate plugs 124a, 124b upon such advancement.

Figure 3B:
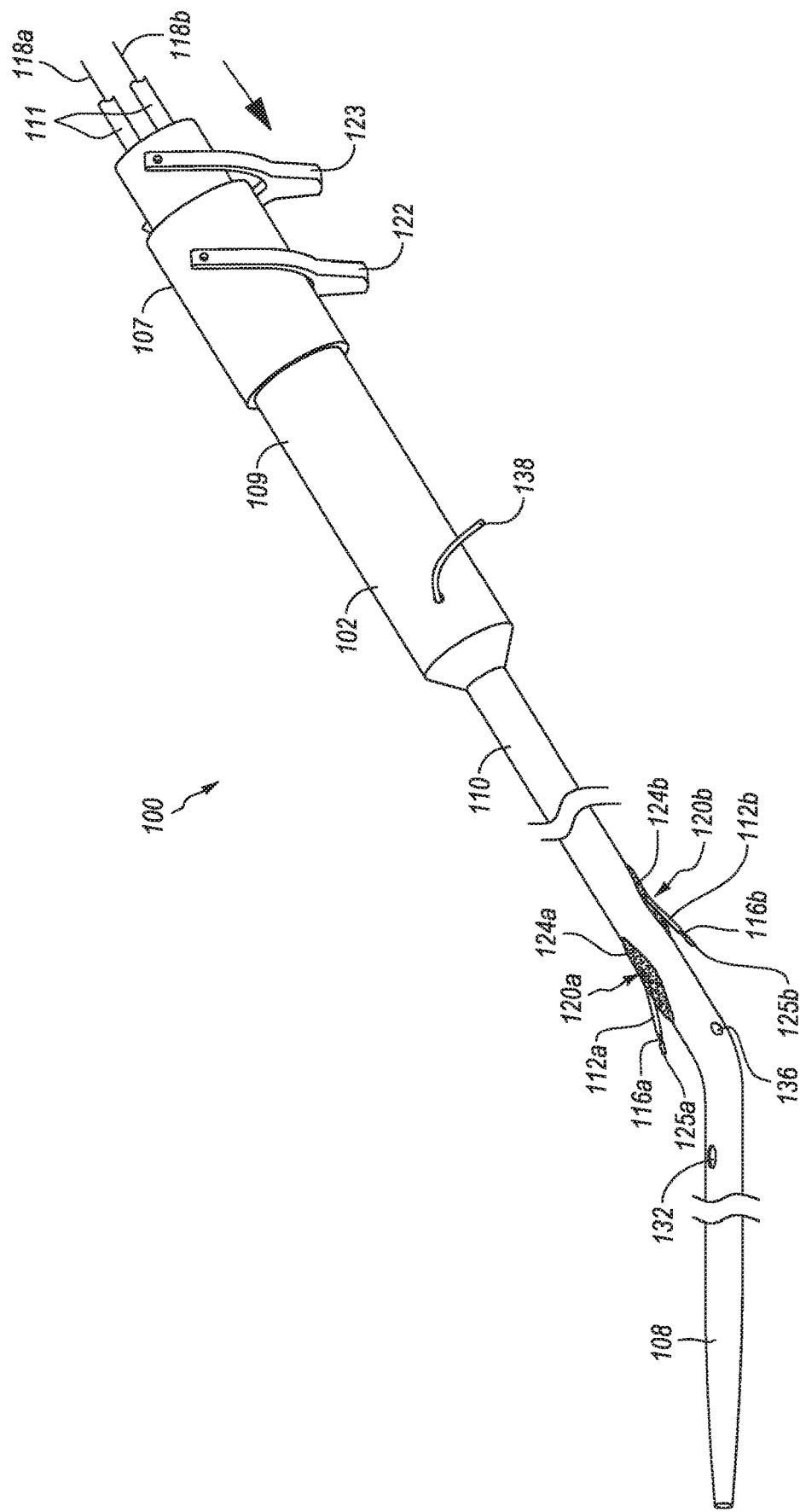
FIG. 3B is an isometric view of the device of FIG. 3A, showing activation of the suture-anchor ejection assembly and associated deployment of the suture-anchor out the distal end of the hollow needles.

As seen in FIG. 3B, upon activation of a suture-anchor ejection assembly (e.g., a coupling mechanism operatively coupling suture-anchor ejection lever 123 with mandrels 116a, 116b), mandrels 116a, 116b are advanced within hollow needles 112a, 112b, pushing the suture-anchor ahead of the respective mandrel, eventually pushing suture-anchors 125a, 125b out of hollow needles 112a, 112b, clear of plugs 124a, 124b.

Figure 5A:
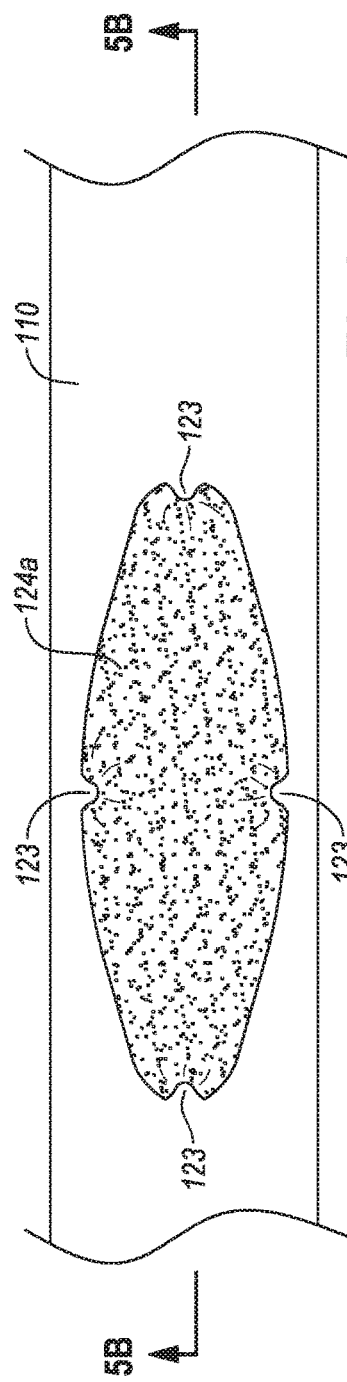
FIG. 5A is a close-up isometric view showing the portion of the needle guide surrounding a needle port and hemostatic plug.
Figure 5B:
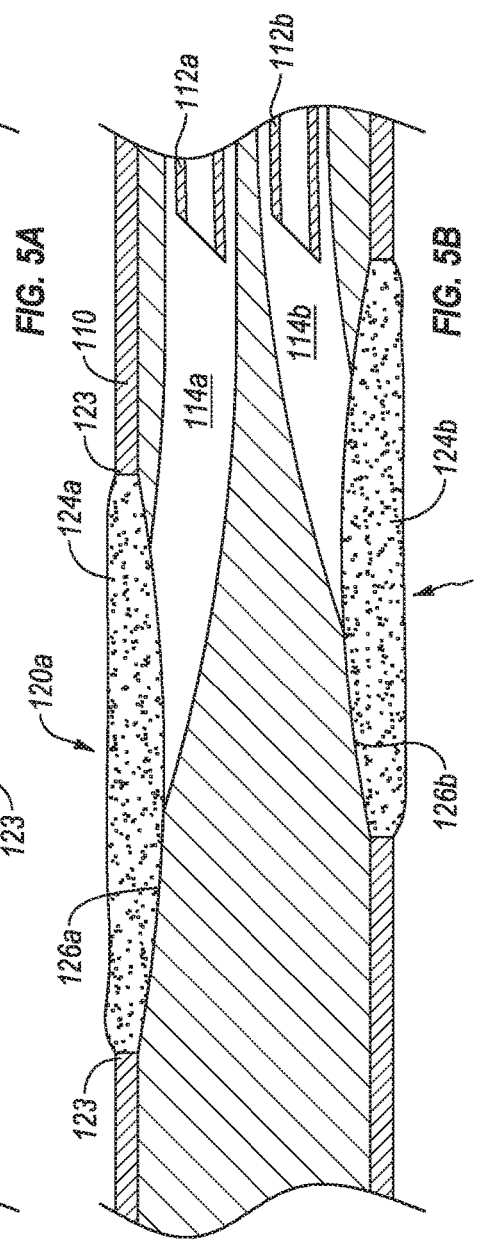
FIG. 5B is a cross-sectional view through the portion of the needle guide shown in 5A.
Figure 5C:
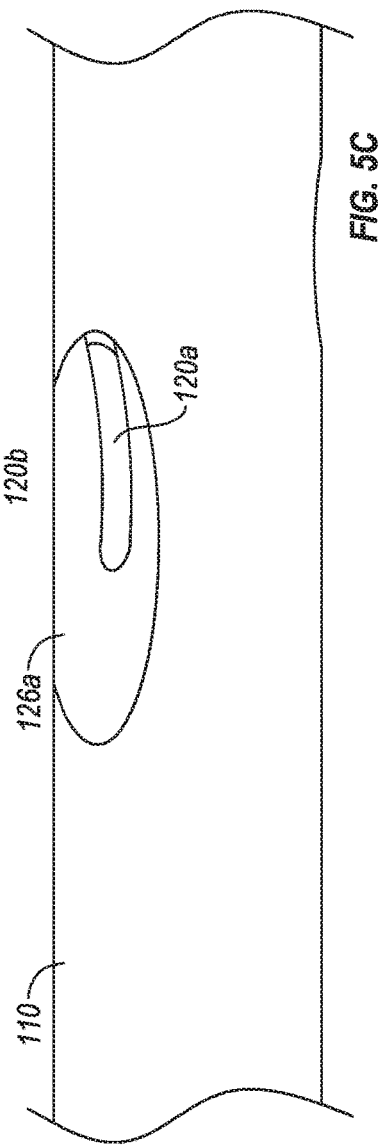
FIG. 5C is a close-up isometric view similar to that of FIG. 5A, showing a portion of the needle guide surrounding a needle port, but in which the hemostatic plug has been removed so as to more clearly show the needle port and surrounding receiving recess into which the hemostatic plug is received.

Device 100 further includes at least one hemostatic plug disposed over the one or more needle ports (e.g., positioned within a receiving recess disposed about the needle port(s). Illustrated device 100 includes two hemostatic plugs 124a and 124b, disposed over needle ports 120a and 120b, within recesses 126a and 126b. FIGS. 5A-5C show close-up views of needle guide 110 in the region surrounding hemostatic plugs 124a, 124b, ports 120a, 120b, and receiving recesses 126a, 126b.

As shown in FIG. 5A, hemostatic plug 124a may be initially retained within receiving recess 126a through any suitable mechanism. In an embodiment, one or more mechanical retention mechanisms such as détentes 123 or other overhanging structure may aid in initially retaining plug 124 within recess 126a. For example, one or more protrusions and corresponding mating recesses may be provided within the retaining recess and hemostatic plug received therein for inhibiting premature dislodgement of the hemostatic plug. In an embodiment, the bottom of receiving recess 126a might include protrusions (e.g., including a bulbous head with an undercut) or recesses (e.g., oppositely configured with an undercut) in which portions of the plug 124a may reside, resulting in increased retention of the plug. Where the plug is a highly flexible putty-like material (e.g., collagen), it may easily adapt into and around such undercuts or other features configured to increase retention force. In another embodiment, a weak adhesive may be applied between the recess 126a and plug 124a to help hold it in place. In any case, the retention force exhibited by the arrangement may be such that the plug is dislodged from recess 126a upon penetration of plug 124a by needle 112a so that upon subsequent withdrawal of needle 112a, plug 124a is dislodged from recess 126a, becoming engaged with suture 118a. While described in the context of hemostatic plug 124a, it will be understood that hemostatic plug 124b may be similarly configured.

As seen in FIG. 5B, ports 120a and 120b may be longitudinally offset relative to one another such that one port (e.g., port 120a) may be disposed anteriorly or distally relative to the other port (e.g., port 120b). Associated structures (e.g., hemostatic plugs 124a, 124b, and receiving recesses 126a, 126b may similarly be longitudinally offset as shown in the figures.

Needle lumen 114a guides hollow needle 112a to exit port 120a at an angle. For example, the distal portion of needle lumen 114a adjacent port 120a may be ramped, as perhaps best seen in FIG. 5B to bias needle 112a to a desired angle relative to the longitudinal axis of needle guide 110, forcing hollow needle 112a to penetrate the tissue adjacent the access passageway during use. Such angle may typically be from about 5° to about 60°, from about 10° to about 45°, or from about 15° to about 35°. Needle lumen 114b may be similarly configured to provide an opposite guiding angle, forcing one hollow needle to penetrate to one side of the access passage, while the other needle penetrates to the other side of the access passage, as shown in FIG. 6C.

Additional details of various needle guide and needle configurations are disclosed in U.S. Publication 2009/0088779 which describes suture delivery and retrieval systems including needle deployment to either side of an access opening. The above application describes configurations that employ an articulating foot into which the needles are received during use. The presently described embodiments rather do not require the use of an articulating foot or any associated control lumen. Rather, the needle guide and sheath portions disposed distal to the receiving recesses 126a, 126b and ports 120a, 120b may be substantially smooth, without the need for any such articulating foot. U.S. Publication 2009/0088779 is herein incorporated by reference in its entirety.

Figure 6A:
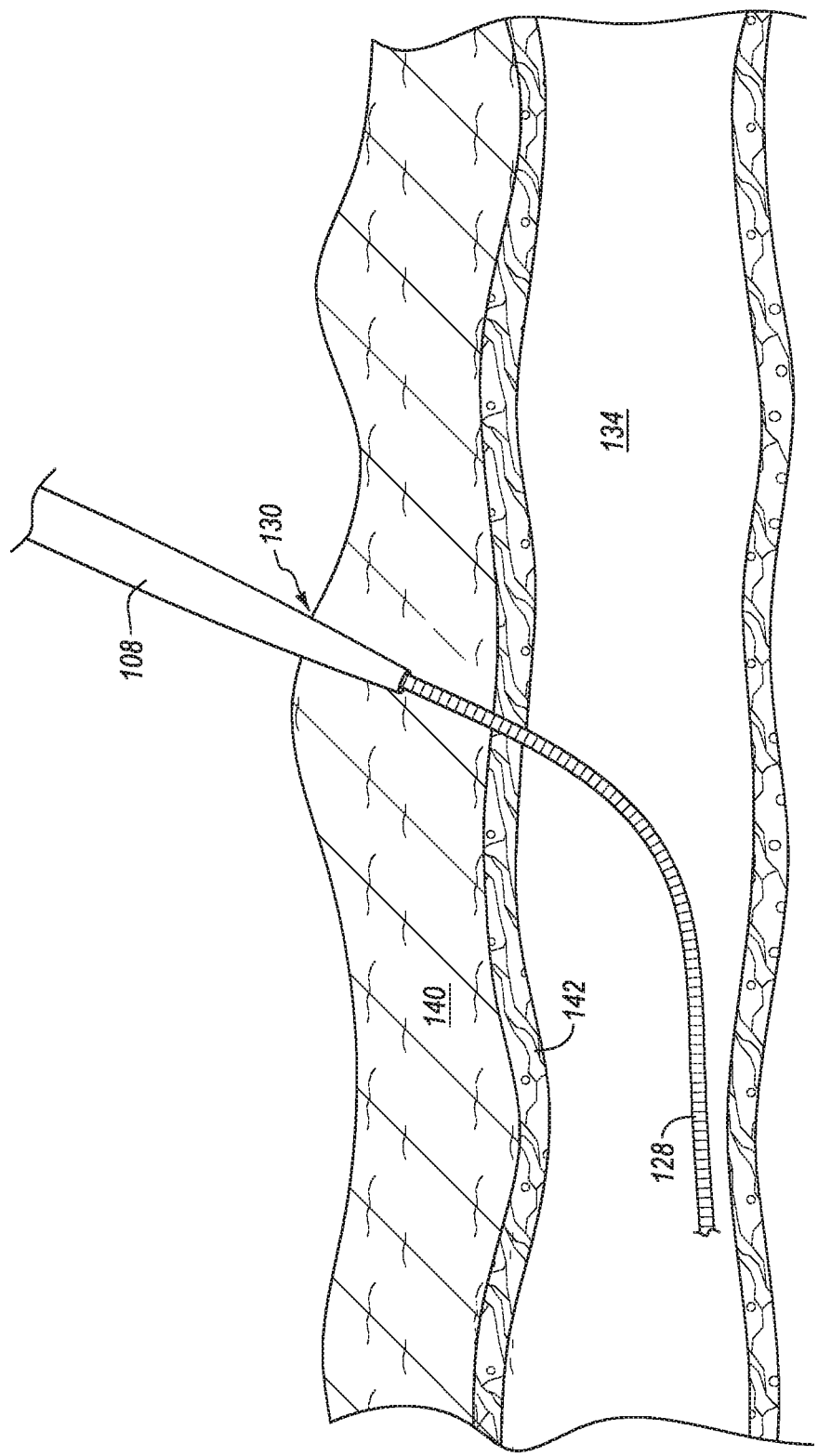
FIGS. 6A-6E illustrate a method for use of the closure device in placing sutures and hemostatic plugs in preparation for closing the access tract.
Figure 6B:
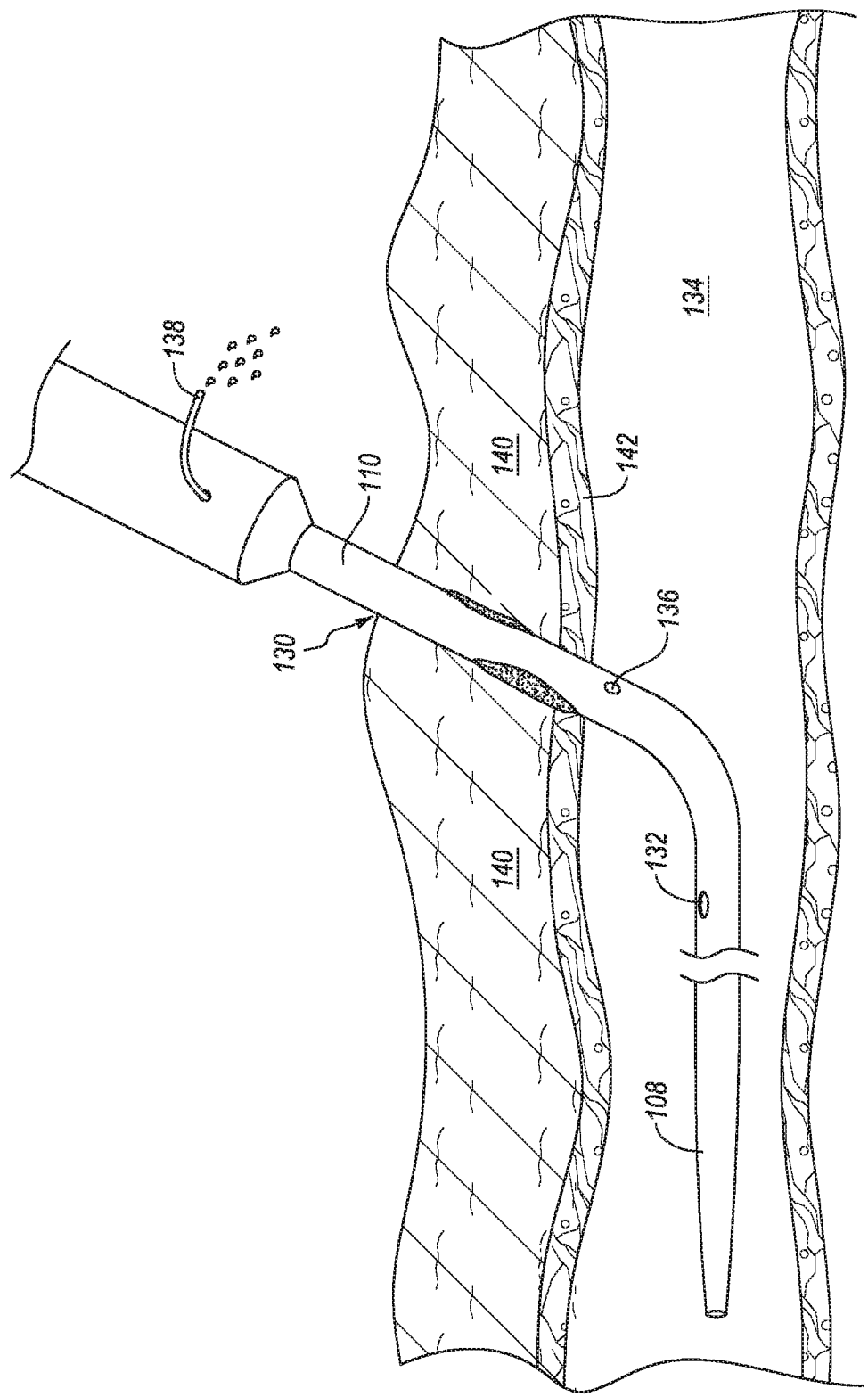

FIGS. 6A-9B illustrate an example of a method for closing an access passageway using device 100. As seen in FIG. 6A, catheter sheath 108 is backloaded over guide wire 128. Sheath 108 and device 100 may be advanced through access tract 130 until guide wire 128 emerges at monorail port 132 (monorail port 132 may be seen in FIG. 1), with sheath 108 positioned within body lumen 134. Monorail port 132 may allow withdrawal of guide wire 128 from body lumen 134 (e.g., an artery) in preparation for closure of access tract or passageway 130. Device 100, including sheath 108 may be advanced within access passageway 130 until marker port 136 is positioned within body lumen 134. Indication that marker port 136 is properly positioned may be indicated by a strong pulsatile flow of blood out marker lumen 138, as seen in FIG. 6B. It is at this position that device 100 may be stabilized in preparation for closing access passageway 130.

Figure 6C:
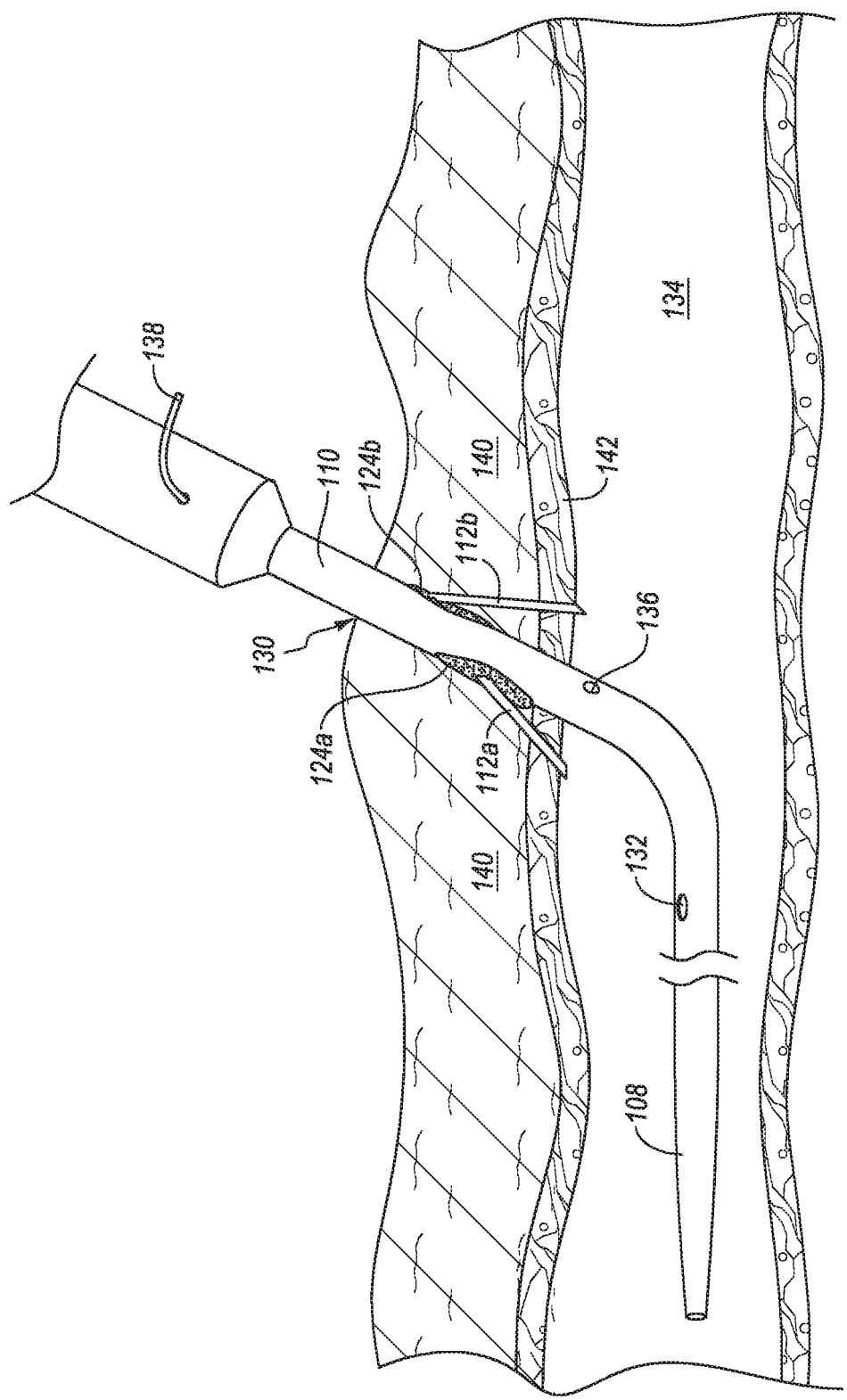

As shown in FIGS. 3A and 6C, needle advancement assembly may be activated (e.g., by pressing lever 122). This action deploys hollow needles 112a and 112b through ports 120a and 120b, as well as through hemostatic plugs 124a and 124b disposed thereover. The hollow needles 112a, 112b are deflected, deploying through the tissue 140 adjacent passageway 130 and through the wall 142 of body lumen 134. Hollow needles 112a and 112b provide access into body lumen 134 through which a suture and associated suture-anchor may be introduced for closing access passageway 130.

Figure 6E:
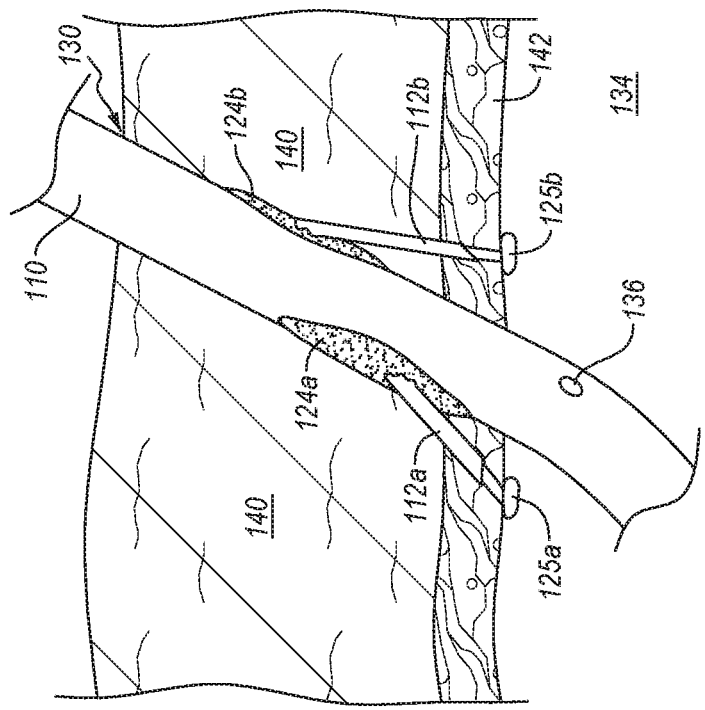
Figure 6D:
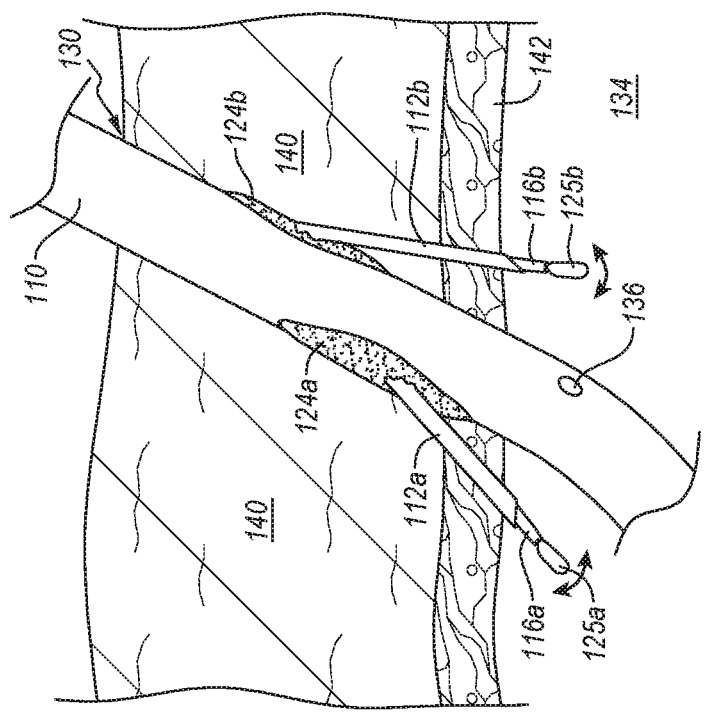

As shown in FIGS. 3B and 6D, the suture-anchor ejection assembly may be activated (e.g., by pressing lever 123), causing advancement of suture-anchor ejection mandrels 116a and 116b within hollow needles 112a and 112b. As shown in FIG. 6D, during this ejection procedure, hollow needles 112a and 112b may remain deployed (e.g., lever 122 remains depressed or otherwise activated). Mandrels 116a and 116b push before them suture-anchors 125a and 125b, so as to push suture-anchors 125a and 125b out hollow needles 112a and 112b into body lumen 134.

Suture-anchors 125a and 125b may be configured to be deployed into body lumen 134 and abut internal wall 142 of lumen 134. For example, suture-anchors 125a and 125b may be elongated with a cross-section sufficiently small to pass through hollow needles 112a, 112b (e.g., pushed by mandrels 116a, 116b), but with a dimension sufficient to bridge the lumen of hollow needles 112a, 112b once rotated after deployment. FIG. 6E shows suture-anchors 125a, 125b in a deployed configuration, so that their longitudinal dimension (which is longer than their transverse width) is transverse to hollow needles 112a, 112b and mandrels 116a, 116b. Suture-anchors 125a and 125b may be deployed in this configuration by simply applying slight tension to sutures 118a and 118b, the distal ends of which are attached to corresponding suture-anchors 125a and 125b. For example, in an embodiment the sutures 118a, 118b may be attached to a side of the corresponding suture-anchor so that as the suture anchor is pushed through the corresponding hollow needle, it maintains its longitudinal orientation.

Because of the attachment point of suture 118a, 118b with the corresponding suture-anchor, once the suture-anchor exits the hollow needle and tension is applied to the suture, the suture anchor may rotate or "gimbal" to assume a rotated (e.g., 90°) orientation, as illustrated by the arrow in FIG. 6D. In the rotated configuration, the major surface area surface of the suture-anchor can be pulled up, adjacent the wall 142 of the body lumen 134. For example, the proximal ends of sutures 118a,118b may be accessible to the practitioner through the proximal end 104 of device 100. By tensioning sutures 118a, 118b and slightly retracting device 100 while maintaining activation of the suture-anchor ejection assembly, the suture-anchors 125a and 125b can be engaged against wall 142 of body lumen 134.

Additional detail of exemplary suture-anchors and their attachment to sutures may be found in U.S. patent application Ser. Nos. 12/684,400, 12/684,542, 12/684,569, 12/684,562, 12/684,470, 13/112,618, and 13/112,631. Each of the above patent applications claim priority to U.S. Provisional Patent Application No. 61/143,751. Each of the above applications is incorporated herein by reference, in its entirety.

Hemostatic plugs 124a, 124b may comprise any suitable material. In an embodiment, such plugs comprise collagen. In another embodiment, such plugs may comprise one or more polymers, such as PEG. Bioabsorbable polymers may be suitable for use (e.g., polylactic acid, polyglycolic acid, copolymers thereof, etc.). Hemostatic plugs 124a, 124b may be swellable, so as to swell as they absorb blood, water, or body fluids present.

Suture-anchors 125a, 125b may comprise any suitable material. In an embodiment, such suture-anchors may be bioabsorbable. As suture-anchors remain behind within body lumen 134, the suture-anchor may comprise a rapidly-eroding material, so as to erode or dissolve within the body lumen 134 within a matter of hours. In an embodiment, the rapidly-eroding material may be a surface eroding material. In particular, the rapidly-eroding material may dissolve from the outer layer inward, thereby preserving the strength of the core of the rapidly-eroding material during the initial stages of dissolution. In one embodiment, this may be similar to the dissolution of a hard candy, wherein dissolution occurs at the outer surface, one layer at a time, rather than dissolving from within.

The rapidly-eroding material may include, in one example embodiment, one or more sugars, such as glucose or sucrose. In a further embodiment, additional materials may be added to the rapidly-eroding material to provide additional properties to the rapidly-eroding material. For example, a polyvinyl pyrrolidone or similar material may be added to enhance toughness, a hyaluronic acid, dextran, and/or similar materials may be added to increase hemocompatibility and thromboresistance, and/or beneficial agents, such as anti-inflammatories, can be added to reduce local scar formation. Heparin may also be added to the rapidly-eroding material when compatible processing temperatures are employed. In a further embodiment, the rapidly-eroding material may include a hydrogel-like material. In a yet further embodiment, the rapidly-eroding material may be coated with a heparin surface treatment, such as benzalkonium heparin.

In one embodiment, the rapidly-eroding material can be configured to be at least partially porous and/or microporous. Accordingly, one or more beneficial agents can be incorporated into at least one of the pores of the rapidly-eroding material. For example, the beneficial agents may include anti-clotting agents, such as heparin, anti-inflammatory agents, and/or other beneficial agents. One method for producing a porous rapidly-eroding material may include freeze drying the rapidly-eroding material. In particular, in one example embodiment, acetic acid may be used as a solvent for freeze drying the rapidly-eroding material. Polymers, such as PLGA, which are soluble in acetic acid, may be used as part of the freeze-drying process.

In a further embodiment, a micro-porous silicon may be used. In particular, the micro-porous silicon may be prepared with various degradation rates, including rapidly degrading forms. The micro-porous silicon may be sufficiently strong to be used in a suture-anchor, and/or may also have sufficient porosity to allow incorporation of beneficial agents. For example, in one embodiment, it may be desirable to incorporate a hydrophobic heparin derivative, such as benzalkonium heparin, into the porosity of the suture-anchor because of its low solubility.

In a yet further embodiment, the suture-anchor may comprise a nano material (e.g., peptides). Once a suture-anchor is deployed within a lumen, the nano-material may dissolve into the fluid flow within the lumen. In particular, the suture-anchor may be configured to dissolve and/or disappear once the suture-anchor is no longer needed.

Figure 7A:
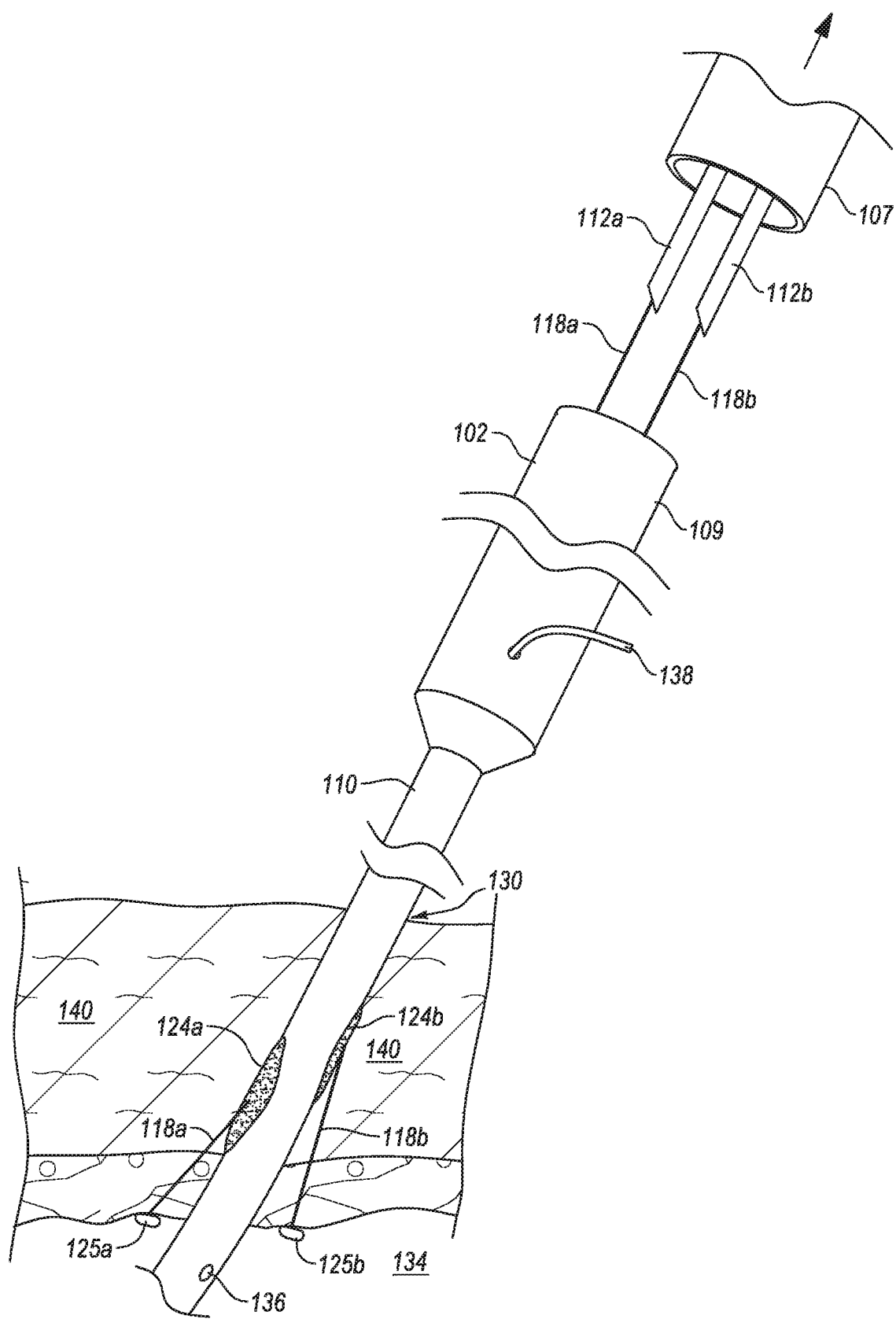
FIGS. 7A-7B illustrate progressive removal of the device from an access tract in preparation for closure of the access tract with the sutures and hemostatic plugs once the sutures have been set.

As seen in FIG. 7A, once suture-anchors 125a, 125b are engaged against wall 142, the proximal portion 107 of device 100, including levers 122 and 123, as well as associated hollow needles 112a, 112b, and suture-anchor ejection mandrels 116a, 116b activated thereby can be retracted from the remaining distal portion 109 of housing 102 of device 100. For example, body 102 may include proximal and distal housing portions 107 and 109 which are detachable from one another. For example, the proximal housing portion 107 may slide over the distal housing portion 109, as shown. Any desired retention mechanisms (e.g., détentes, couplings, etc.) may be included to initially couple the two portions together and prevent inadvertent premature separation of the proximal housing portion from the distal housing portion. In an embodiment, any coupling of the two portions may be such that upon separation, the separation is irreversible (e.g., breaking or fracture of a coupling mechanism). In another embodiment, the coupling mechanism may allow recoupling of the separated portions (i.e., separation may be reversible).

Figure 7B:
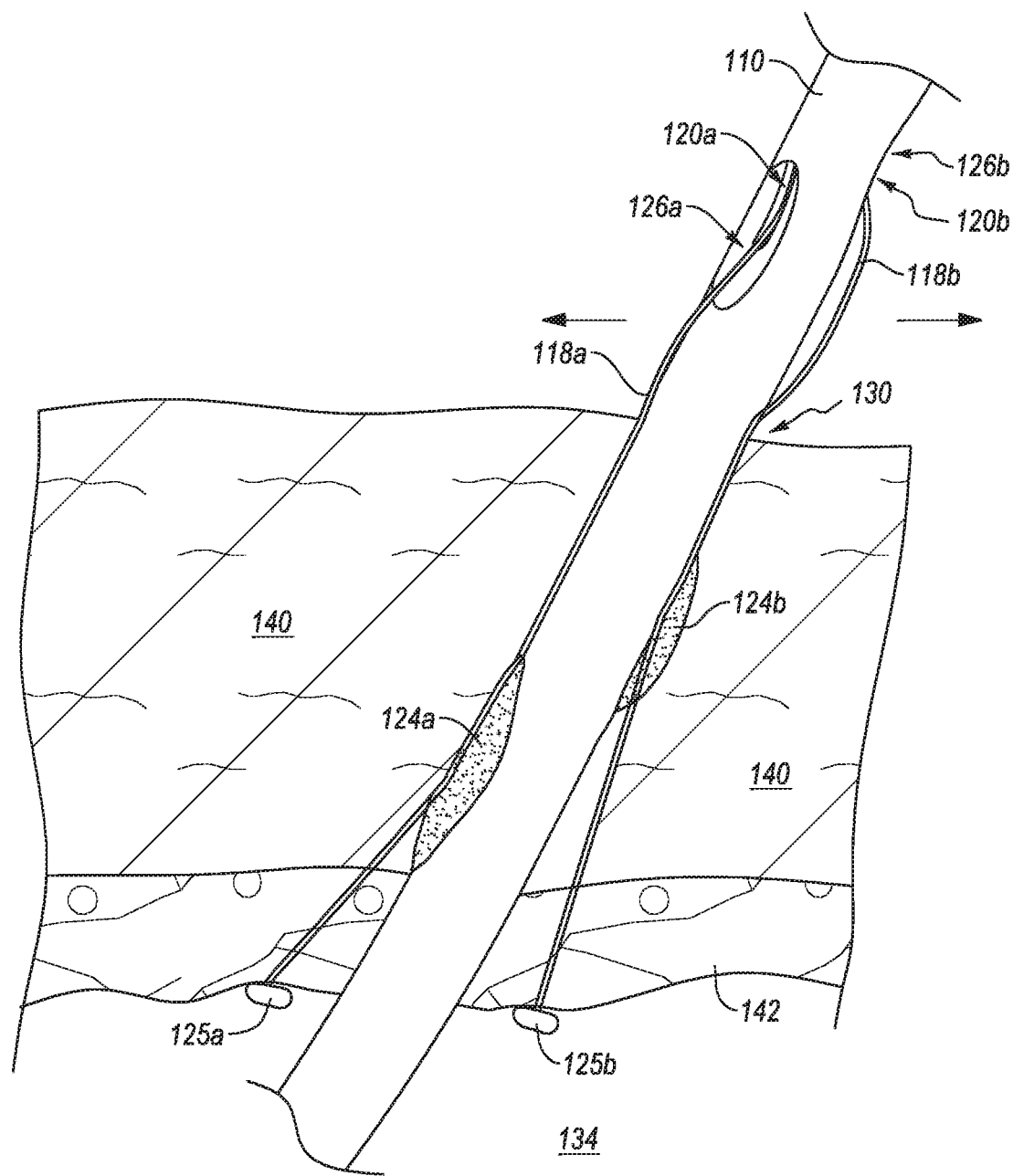

As the proximal portion 107 of the device 100 is removed, sutures 118a and 118b remain behind, with distal portion 109 of device 100. As seen in FIG. 7B, the distal portion 109 of device 100, including attached needle guide 110 and sheath 108, may then be partially retracted from access passage 130 so that sheath 108 maintains hemostasis of access passage 130, while the proximal legs of sutures 118a and 118b are harvested from needle ports 120a and 120b (e.g., by pulling sutures 118a and 118b laterally outward as indicated by the arrows in FIG. 7B).

As described above, the adherence strength of hemostatic plugs 124a and 124b within recesses 126a and 126b may be such that penetration of hemostatic plugs 124a, 124b by needles 112a, 112b is sufficient to dislodge plugs 124a, 124b from recesses 126a, 126b. As a result, when distal portion 109 is partially retracted as seen in FIG. 7B, hemostatic plugs are retained at the location within access passage 130 where they were penetrated by needles 112a and 112b. Although needles 112a and 112b have been retracted as seen in FIG. 7B, sutures 118a and 118b maintain in their prior position, passing through plugs 124a and 124b, and helping to retain plugs 124a and 124b in place as needles 112a and 112b are retracted.

Figure 8A:
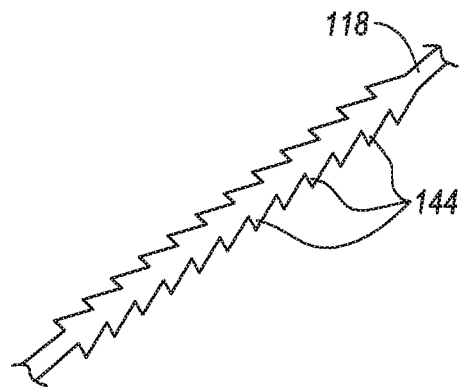
FIGS. 8A-8C illustrate how the sutures may include barbs to resist movement of the hemostatic plug once the barbed suture engages the plug.
Figure 8B:
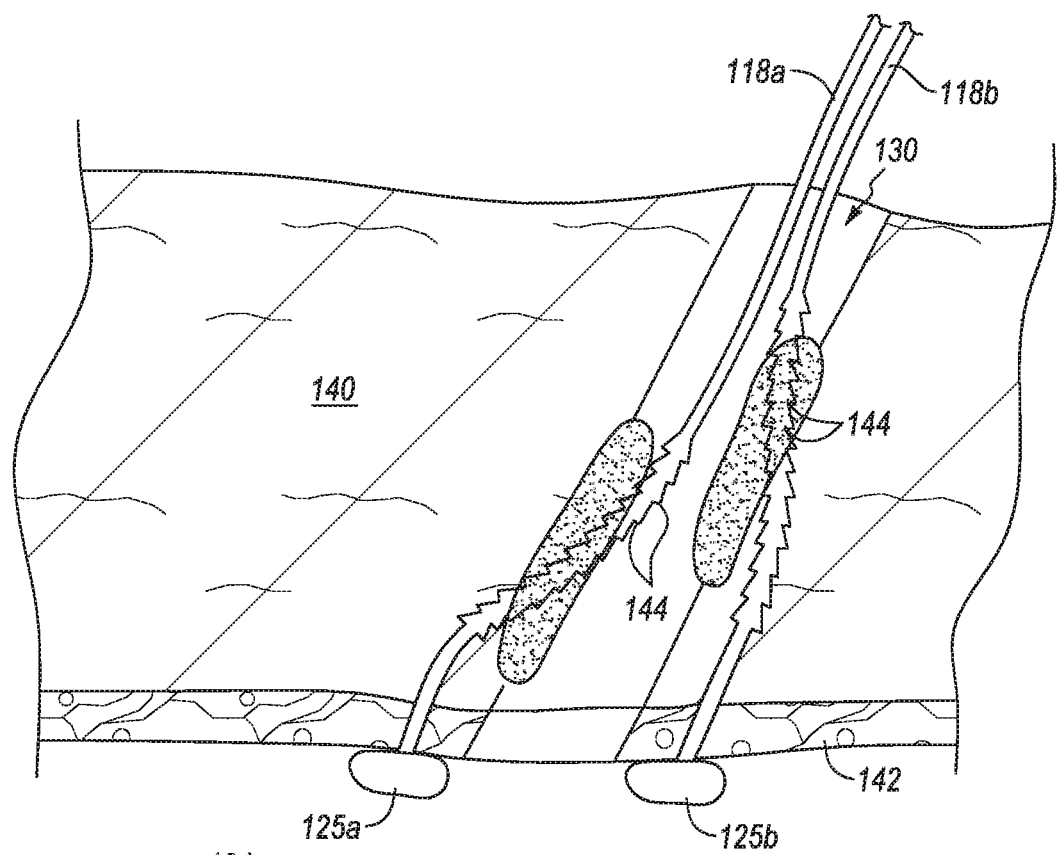

In an embodiment, sutures 118a and 118b may include at least a portion thereof that is specially configured to aid in retaining hemostatic plugs 124a and 124b in place. For example, FIGS. 8A and 8B illustrate a suture 118 including one or more barbs 144 configured to resist proximal movement of plugs 124a, 124b once suture 118 is engaged therewith. Adjacent portions of suture 118, away from plugs 124a, 124b, may be smoother than the barbed section. Illustrated barbs 144 include a wider distal dimension or ledge, which tapers to a smaller proximal dimension. The illustrated barb configuration is merely exemplary, and other configurations may also be suitable for use. In another embodiment, suture 118 may be etched or otherwise chemically or mechanically treated (e.g., by abrasion) to provide a roughened surface to at least a portion of suture 118, providing a similar retention characteristic. As employed herein, the term "barbed" as relating to the suture is to be broadly construed to encompass such treatments or manufacturing techniques resulting in a roughened surface.

Figure 8C:
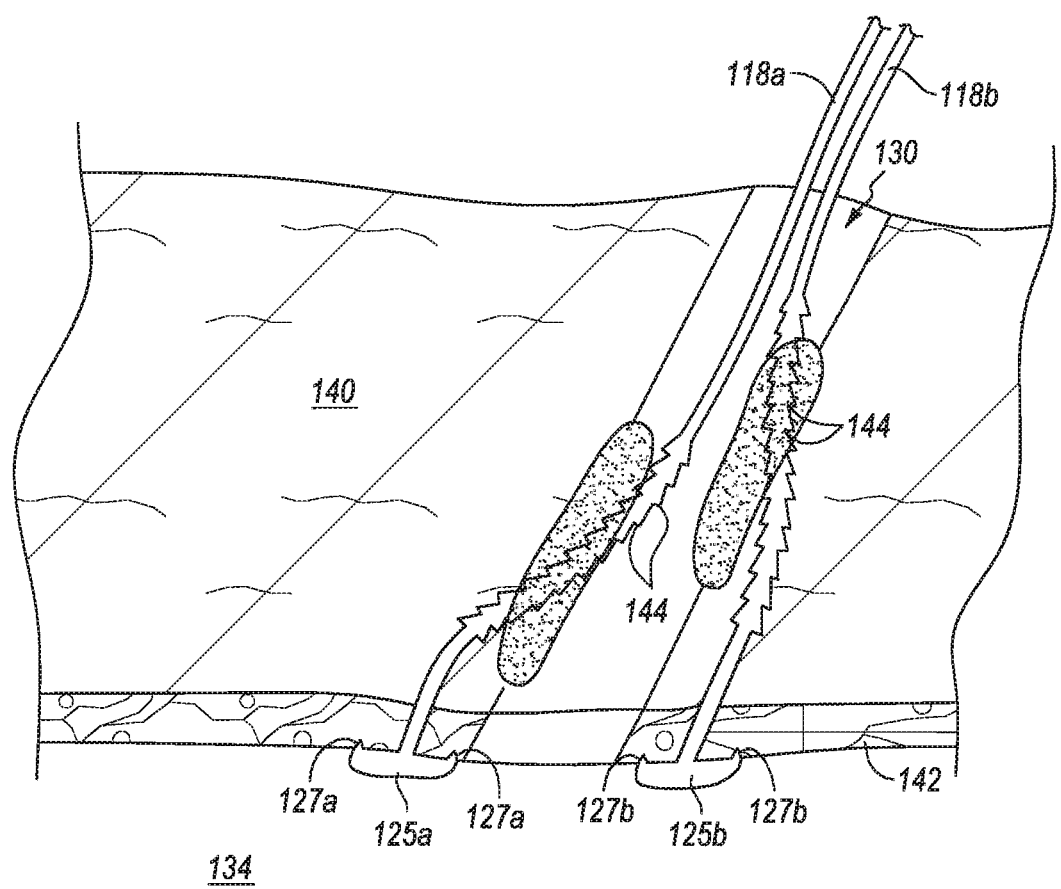

In an embodiment, barbs may similarly be provided on hollow needles 112a, 112b in order to aid in dislodging and pushing hemostatic plugs 124a, 124b from receiving recesses 126a, 126b. Such barbs may also be provided on suture-anchors 125a, 125b. FIG. 8C illustrates an embodiment where suture-anchors 125a and 125b each include one or more barbs 127a, 127b, respectively, to aid in stabilization. For example, the surface of each suture-anchor that becomes oriented in apposition to body lumen (e.g., artery) wall 142 may include one or more barbs for engagement with wall 142, stabilizing the suture-anchor in the desired orientation and position.

The suture-anchors may be of a one-piece type construction, or may comprise two or more pieces joined (e.g., mechanically) together. The suture-anchors may vary in length, mass, or other characteristics to facilitate ejection and gimballing.

As seen in FIG. 9A, a surgical knot (e.g., such as the surgical sliding knot shown) may be tied, and device 100 may be fully retracted from access passage 130 as the knot is advanced (FIG. 9B), pulling tissue 142 in apposition, closing passage 130. Because of the presence of hemostatic plugs 124a and 124b engaged on suture legs 118a and 118b, a secondary sealing mechanism is provided through the hemostatic plug material, providing a more effective closure of opening 130 as compared to suture or a hemostatic plug alone.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for closing an opening in tissue, the device comprising:
   a delivery shaft;
   an anchor deployable from the delivery shaft, the anchor comprising an elongate body with a plurality of stabilizing members that extend proximally in a deployed state;
   a suture attached to the anchor and extending from the anchor at a location intermediate a proximal end and a distal end of the anchor, the anchor extending transversely to a longitudinal axis of the anchor in the deployed state; and
   a deployment mandrel configured to directly contact the anchor during deployment and being selectively distally advanced to advance the anchor from the delivery shaft, the plurality of stabilizing members are configured to stabilize the anchor against the tissue.

2. The device of claim 1, wherein the anchor is rotatably mounted to the suture.

3. The device of claim 1, wherein the suture extends transversely to a surface of the anchor.

4. The device of claim 1, wherein the delivery shaft comprises a lumen for the anchor.

5. The device of claim 1, wherein the delivery shaft comprises a side exit opening through which the anchor extends.

6. A device for closing an opening in tissue, the device comprising:
   a delivery shaft;
   a plurality of one-piece suture-anchors configured to be deployed from the delivery shaft, each suture-anchor comprising an elongate body with a plurality of barbs that extend proximally in a deployed state;
   a suture portion associated with each one-piece suture anchor, the suture portion being attached to the anchor and extending from the anchor at a location intermediate a proximal end and a distal end of the anchor, the anchor extending transversely to a longitudinal axis of the anchor in the deployed state; and
   a plurality of deployment mandrels each associated with a one-piece suture-anchor of the plurality of one-piece suture-anchors, the deployment mandrels being configured to directly contact the anchor between the plurality of barbs that extend from the anchor during distal movement during deployment and being selectively distally advanced to advance the plurality of one-piece suture-anchors from the delivery shaft, the plurality of barbs being configured to stabilize the anchor against the tissue.

7. The device of claim 6, wherein the one-piece suture-anchor is gimbally mounted to the suture portion.

8. The device of claim 6, wherein the delivery shaft comprises a plurality of lumens, each lumen receiving one one-piece suture-anchor of the plurality of one-piece suture-anchors.

9. The device of claim 6, wherein the delivery shaft comprises a lever that selectively moves the plurality of mandrels.

10. The device of claim 6, wherein the delivery shaft comprises a plurality of side exit openings through which the plurality of one-piece suture-anchors extends.

11. A method of closing an opening in tissue, the method comprising:
positioning a delivery device for closing the opening in the tissue adjacent the tissue, the delivery device comprising:
a delivery shaft;
a plurality of one-piece suture-anchors deployable from the delivery shaft, each suture-anchor comprising an elongate body with a plurality of stabilizing members that extend proximally in a deployed state;
a suture portion associated with each of the plurality of the suture-anchors, the suture portion being attached to the suture-anchor and extending from the suture-anchor at a location intermediate a proximal end and a distal end of the suture-anchor, the suture-anchor extending transversely to a longitudinal axis of the anchor in the deployed state; and
a deployment mandrel associated with each of the plurality of the suture-anchors, the deployment mandrel being configured to directly contact the associated suture-anchor between the plurality of stabilizing members that extend from the suture-anchor during distal movement during deployment and being selectively distally advanced to advance the suture-anchor from the delivery shaft, the plurality of stabilizing members are configured to stabilize the suture-anchor against the tissue;
deploying the plurality of one-piece suture-anchors into the tissue near the opening; and distally advancing a knot in the suture associated with the plurality of one-piece suture-anchors to pull the tissue into apposition, closing the opening.

12. The method of claim 11, further comprising moving the plurality of one-piece suture-anchors towards the opening as the knot is distally advanced.

13. The method of claim 11, wherein deploying the plurality of one-piece suture-anchors comprises actuating a lever to distally advance the plurality of mandrels associated with the plurality of one-piece suture-anchors.

14. The method of claim 11, wherein a one-piece suture-anchors of the plurality of one-piece suture-anchors is rotatable relative to the suture.

15. The method of claim 11, wherein the plurality of stabilizing members is a plurality of barbs.

16. The method of claim 11, wherein the delivery device comprising a plurality of lumens each accommodating one of the plurality of one-piece suture-anchors.

17. The method of claim 16, wherein deploying the plurality of one-piece suture-anchors further comprises actuating a lever to advance the plurality of one-piece suture-anchors through the plurality of lumens.

18. The method of claim 17, wherein deploying the plurality of one-piece suture-anchors comprises penetrating the tissue with a plurality of hollow needles before deploying the plurality of one-piece suture-anchors toward the tissue.

19. The method of claim 11, wherein deploying the plurality of one-piece suture-anchors comprises deploying the plurality of one-piece suture-anchors at an angle into the tissue.

\* \* \* \* \*